United States Patent [19]

Taneja et al.

[11] Patent Number: 5,629,351

[45] Date of Patent: May 13, 1997

[54] BOSWELLIC ACID COMPOSITIONS AND PREPARATION THEREOF

[75] Inventors: Subhash C. Taneja; Vijay K. Sethi; Kanaya L. Dhar; Randhir S. Kapil, all of Jammu, India

[73] Assignee: Council of Scientific & Industrial Research, New Delhi, India

[21] Appl. No.: 421,500

[22] Filed: Apr. 13, 1995

[51] Int. Cl.$^6$ .................................................. A61K 31/015

[52] U.S. Cl. ...................... 514/765; 514/766; 514/886; 514/925

[58] Field of Search ..................... 424/195.1; 514/766, 514/574, 765, 886, 925; 260/388 R

[56] References Cited

U.S. PATENT DOCUMENTS 5,064,823  11/1991  Lee et al. ................................ 514/198

OTHER PUBLICATIONS

"The Stereochemistry Of The Boswellic Acids", G. Graham Allan, Phytochemistry, 1968, vol. 7, pp. 963–973. Pergamon Press. Printed in England.

"Anti–Arthritic Activity Of Boswellic Acids In Bovine Serum Albumin (BSA)–Induced Arthritis", M.L. Sharma, S. Bani and G.B. Singh, Int. J. Immunopharmac., vol. 11, No. 6, pp. 647–652, 1989.

"Effect of Salai Guggal Ex–Boswellia Serrata On Cellular And Humoral Immune Responses And Leucocyte Migration", M.L. Sharma, A. Khajuria, A. Kaul, Surjeet Singh, G.B. Singh and C.K. Atal, Agents and Actions, vol. 24, 1/2 (1988).

"254. Zur Kenntnis der Triterpene.", Volumen XXXII, Fasciculus VI (1949)–No. 254, pp. 1911–1921.

"XIII Annual Conference Of IPS", pp. 59 & 63.

"Pharmacology Of An Extract Of Salai Guggal Ex–Boswellia Serrata, A New Non–Steroidal Anti–Inflammatory Agent", G.B. Singh and C.K. Atal, Agents and Actions, vol. 18, 3/4 (1986).

"Inhibition Of Leukotriene $B_4$ Formulation in Rat Peritoneal Neutrophils By An Ethanolic Extract Of The Gum Resin Exudate Of Boswellia Serrata", H.P. T. Ammon, T. Mack, G.B. Singh and H. Safayhi, Planta Medica, Paper 31/7905 (Pharmacology).

B. Mahajan, et al., Two Triterpenoids From Boswellia Serrata Gum Resin, Phytochemistry, 39(2):453–455 1995.

*Primary Examiner*—John W. Rollins
*Attorney, Agent, or Firm*—Dale Lynn Carlson; Wiggin & Dana

[57] ABSTRACT

Disclosed herein is a novel fraction comprising a mixture of boswellic acids, wherein the fraction exhibits anti-inflammatory and antiulcerogenic activities. Also disclosed is a novel boswellic acid compound exhibiting anti-inflammatory, antiathritic and antiulcerogenic activities. Also disclosed is a process for isolating a boswellic acid fraction and individual boswellic acids therefrom.

9 Claims, No Drawings

BOSWELLIC ACID COMPOSITIONS AND PREPARATION THEREOF

FIELD OF THE INVENTION

The invention relates to a novel boswellic acids isolated from the gum resin of the plant *Boswellia serrata* Roxb. (Burseraceae).

BACKGROUND OF THE INVENTION

The gum resin of the plant *Boswellia serrata* Roxb. (Burseraceae) has long been in use for the treatment of rheumatoid arthritis and gout by the practitioners of Ayurvedic medicines in the Indian system of medicine. Various extracts of the gum resin have shown potent anti-flammatory and anti-arthritic activity in laboratory animals, as well as during clinical trials ((Atal, C. K., Singh, G. B., Batra, S. and Gupta, O. P., Ind. J. Pharm, 12, 59 (1980); Pachnanda, V. K. Shahikant, Singh, D. and Singh, G. B., Ind. J. Pharm, 13, 63 (1981). In a detailed pharmacological study, Singh et al have established that the alcoholic extract of *B. serrata* gum resin displayed marked anti-flammatory activity in carrageenan induced oedema in rats and mice and dextran oedema in rats (Singh, G. B. and Atal. C. K., Agent and Action, 18 407, (1986).

It has also been recognized in the past that the ethanolic extract of the gum resin of *B. serrata* inhibits the formation of Leukotriene B4 in rat peritoneal neurophils. Leukotriene B4 is one of the important mediators of inflammatory reactions [Ammon, H. P. T., Mack, T., Singh, G. B. and Safayhi, H., Planta Medica, 57, 203 (1991).]

The gum resin from *Boswellia serrata* Roxb. (Burseraceae) is a complex mixture of various terpenoids, polysaccharides and inorganic salts. The polysaccharides and inorganic salts constitute one of the major parts of the said gum. The terpenoids part constitute both lower and higher terpenoids. The lower terpenoids which constitute mainly the monoterpenoids are obtained by steam distillation of the gum resin.

The higher terpenoids fraction which is pharmacologically active is a mixture of various di- and triterpenoids. It has now been established that the anti-flammatory activity of this fraction is due to the presence of certain triterpenoids commonly known as boswellic acids. Boswellic acids are penta cyclic triterpenic acids belonging to the class of ursane group of triterpenoids [Bischof, B, Jerger O, and Ruzicka L., Helv. Chim, Acta, 32, 1911 (1949), and Grham, A. G. Phytochemistry, 7, 963 (1968).]

Two general methods of isolation and separation of boswellic acids from the gum resin of the said plant are chemical and chromatographic. In one of the chemical methods which is described by Winterstein et al [Winterstein, A. and Stein, G., Z. Physiol. Chem., 208,9 (1932) and J. Am. Chem. Soc, 74,3179 (1952)], the gum exudate is extracted with solvent ether and the total acids are precipitated as barium salts using barium hydroxide as the precipitant. The salts obtained are then directly converted into their acetates by heating it with acetic anhydride and pyridine. The boswellic acids The disadvantage of this method is that the acids are not isolated in their natural forms, but are isolated as their acetates.

In the chromatographic method, defatted ethanolic extract of the gum resin of the said plant is subjected to repeated column chromatography over silica gel and elution with organic solvents such as chloroform, methanol in different proportions furnishes individual boswellic acids in pure form.

The method suffers from the disadvantages of being cumbersome, time consuming and unsuitable for large scale preparations.

New boswellic acid compositions, particularly those possessing unexpected therapeutic properties, and methods for the preparation thereof, would be highly desired by research and industry. The present invention provides such a result.

SUMMARY OF THE INVENTION

In one aspect, the present invention relates to a novel fraction exhibiting anti-inflammatory and antiulcerogenic activities, said fraction comprising a mixture of boswellic acids of the formulae I through VI identified as follows:

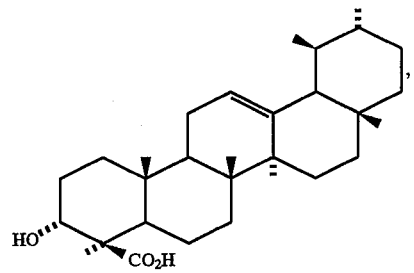

Formula I

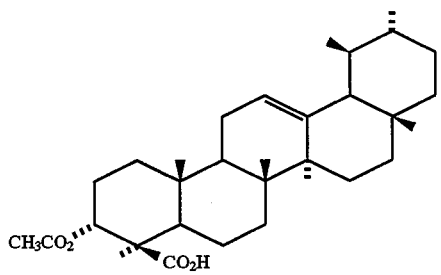

Formula II

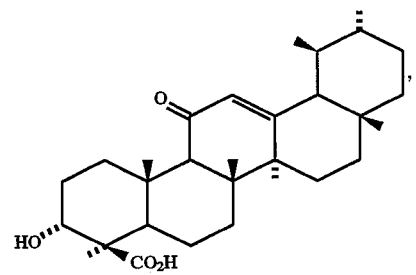

Formula III

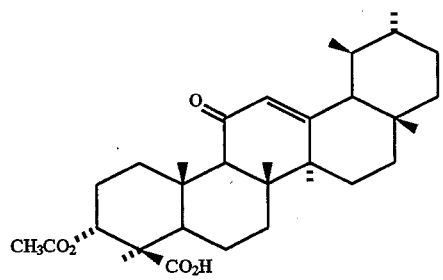

Formula IV

Formula V

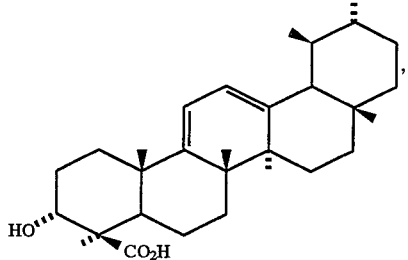

Formula VI

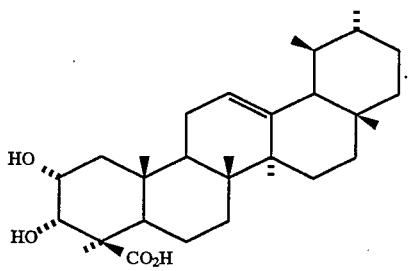

In another aspect, the present invention relates to a boswellic acid compound exhibiting anti-flammatory and antiulcerogenic activities and having the structural formula:

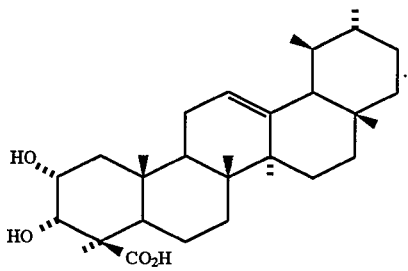

In yet another aspect, the present invention relates to a process for the isolation of a boswellic acid fraction exhibiting anti-flammatory and antiulcerogenic activities, said fraction comprising a mixture of boswellic acids, and optionally isolating individual bsowellic acids from said fraction, said process comprising the steps of:

(a) crushing the lumps of the gum resin of *Boswellia serrata* and extracting the crushed lumps with a polar solvent to provide an extract;

(b) removing insoluble material from said extract;

(c) concentrating the extract till a reddish brown syrupy mass is obtained;

(d) basifying the syrupy mass with an aqueous solution of an alkali to provide a solution having a pH in the range of 9 to 10;

(e) extracting the solution with chlorinated or non-polar solvents to provide an aqueous layer, and acidifying the aqueous layer with mineral acid to a pH in the range of 3–5 to provide a precipitate comprising boswellic acids;

(f) washing the precipitate with water to provide said fraction being neutral to litmus;

(g) drying the fraction to provide a dry fraction; and, optionally, (h) separating individual boswellic acids from said fraction.

These and other aspects will become apparent upon reading the following detailed description of the invention.

DETAILED DESCRIPTION OF THE INVENTION

It has now been surprisingly found that a fraction isolated by the process disclosed in the present invention containing the mixture of boswellic acids comprising mainly six triterpenoic acids namely B-Boswellic acid (3a-hydroxy urs-12 ene-24-oic acid) of the formula I shown above; acetyl B-boswellic acid (3a-acetoxy urs-12-ene-24-oic acid) of formula II; 11-keto-B-boswellic acid (3a-hydroxy urs-12-ene-11-keto-24-oic acid) of formula III; acetyl 11-keto-B-boswellic acid (3a-acetoxy urs-12-ene-11-keto-B-boswellic acid) of formula IV, 3a-hydroxy urs-9, 12-diene-24-oic acid of the formula V, 2a, 3a dihydroxy urs-12-ene-24-oic acid of the formula VI, together with other unidentified compounds.

Five boswellic acids (indentified above as formula I through formula V) are already known from the parent gum for a long time, but earlier attempts were focused on isolation and identification of the individual compounds from a chemistry point of view. In contrast, the present inventors proceeded to indentify an active fraction from the extracts of *Bodwellic serrata*. Once the active fraction was indentified, the present inventors proceeded to indentify and ascertain the individual composition of the main constituents of the fraction. During these studies, we were able to isolate the compound of formula VI which was hitherto unknown. Further, the pharmacological activities associated with the active fraction isolated by the present inventors, containing specified amounts of compounds of formulae I to VI, are particularly surprising.

The Boswellic acid of the formula VI has the following characteristics:

White crytals from petrol ethyl acetate, m.p. 174° C., analyzed for $C_{30} H_{48} O_4$; requires C 76.27, H, 10.0 observed C 75° H., 9.8%, Ir 3460, cm$^{-1}$, 1690, 1480, 1200, 1050, 750; MS m/z 472 [M]$^+$, 218, 203, 194;

1HNMR (CDcl$_3$) S;00.80 (3H, S, Me), 0.94 (6H, M. 2X Me, 1.10) (6H, m, 2x Me), 1.18 (3H, S, Me), 1.38 (3H S Me), 4.08 (1H, brm, H-2), 4.26 (1H, dd, J=12.6 and 2.7 HZ.

The fraction isolated by the process of the present invention has anti-flammatory, anti-arthritic and anti-ulcerogenic activities. Hence, the fraction isolated may be used for the treatment of the above said diseases as such or an admixture or in combination with other known drugs.

Inflammation may be considered as essentially the protective response to any noxious stimulus that may threaten the well being of the host. It may be an acute, transient or highly localized response to a simplest finite event to a complex sustained response involving whole organism. Inflammation can be controlled by anti-flammatory drugs exemplified by phenylbutazone, aspirin, indomethacin, ibuprofen etc. Many of these drugs are synthetic molecules which are quite effective, but their sustained use may result in harmful side effects to the host. Aspirin for example, is the cause of gastric ulceration and allergic reaction.

In the continuing search for new anti-inflammatory drugs, many steroidal and non-steroidal organic molecules have been isolated from the plant sources as well as synthesized in the laboratories. However, an anti-inflammatory compound, insolated from natural sources or derived by the chemical modulation of a natural molecule is yet to find its acceptability as a drug. The need for a safer drug preferably based on a natural compound with no or minimal side affects is therefore imperative.

The present invention satisfies this need and avoids the problem associated with most of the known synthetic drugs which possess anti-inflammatory or anti-arthritic properties, namely that synthetic drugs cause ulceration as a side effect. In contrast, the fraction from *Boswellia serrata* displays significant anti-ulcerogenic activity while avoiding or minimizing the undesireable side effects.

Although not wishing to be bound by any particular theory, the anti-ulcerogenic activity of the said fraction is believed by the present investors to be attributable to the combined synergistic effects of the constituents of the fraction.

The present inventors have extracted and identified a pharmacologically active fraction containing the mixture of the above said boswellic acids of the formulae I through VI, together with some unidentified compounds, the compositions of which suitably comprises (and advantageously consists essential of):

35 to 55% of the formula 1

25 to 45% of the formula 2

4 to 14% of the formula 3

3 to 13% of the formula 4

1 to 3% of the formula 5

3 to 7% of the formula 6 and 3 to 7% other identified compounds, wherein all percents are based upon the weight of the composition.

The amounts of the above said ingredients may vary depending upon the various factors such as time of collection of the gum resin, place, age of the tree, quality of the gum and the like.

Due to the above said combination of the constituents of the fraction, a synergistic effect is imparted to the fraction resulting in the fraction showing a combined anti-inflammatory, anti-arthritic and anti-ulcerogenic activities. Though individual Boswellic acids of the formulae 1 to 5 have been isolated, it is our novel finding according to the present invention that the fraction containing the mixture of boswellic acids of the formulae 1 to 6 together with the unidentified compounds in the above said combination show synergistic combined anti-inflammatory, anti-arthritic and anti-ulcerogenic activities which is hitherto unknown.

One object of the present invention, therefore, is to provide a process for the isolation of a new hoswellic acid having the formula VI shown above.

Another object of the present invention is to provide a process for the isolation of the fraction containing the above said new boswellic acid of the formula VI which can be isolated on a commercial basis.

Accordingly, the present invention provides a new boswellic acid of the formula VI and a novel fraction containing the compounds of the formulae 1 to VI. This novel compound and the fraction is suitably prepared by:

(a) crushing the lumps of the gum resin on *Bowsellia serrata* extracting with a polar solvent;

(b) removing the insoluable material by known methods;

(c) concentrating the extracts under reduced pressure by removing the organic solvent till a reddish brown syrupy mass is obtained;

(d) basifying the syrupy mass with an aqueous solution of an alkali to attain the pH in the range of 9 to 10;

(e) extracting the solution with chlorinated or non-polar solvents and acidifying the aqueous layer with mineral acid to pH in the range of 3–5;

(f) separating the precipitate of the mixture of boswellic acids comprising (3a-hydroxy urs-12-ene-24-oic) of the formula 1 shown in the drawing accompanying this specification, acetyl-B-boswellic acid (3a-acetoxy urs-12-ene-24-oic acid) of formula 2; 11-keto-B-boswellic acid) 3a-hydroxy urs-12-ene-11-keto-24-oic acid) of formula 3; acetyl-11-keto-B-boswellic acid (3a-acetoxy urs-12-ene-11-keto-24-oic acid of the formula 4, 3a-hydroxy urs-9, 12-diene-24-oic acid of the formula 5, 2a, 3a-dihydroxy urs-12-ene-24-oic acid of the formula 6 and other unidentified compounds;

(g) washing several times with water till neutral to litmus;

(h) drying the resultant fraction over anhydrous sodium sulphate or anhydrous calcium chloride; and (i) separating the individual boswellic acids by known methods.

The total yield of the fraction isolated by the process of the invention may vary between 25–35% depending upon the time, place where the plant is grown and the quality of the gum resin and its moisture content.

The polar solvent used in step (a) may be selected from methanol, ethanol, butanol, acetone, ethyl acetate and the like or their mixtures. The aqueous alkali solution used for basifying in step (d) may be selected from sodium hydroxide, barium hydroxide or potassium hydroxide. The chlorinated or non-polar solvent used in step (e) may be selected from dichloromethane, chloroform, dichloromethane, hexane, petroleum ether, benzene and the like or their mixtures. The mineral acid used in step (e) may be selected from hydrochloric acid, sulphuric acid and the like.

The separation in steps (b) and (f) may be effected filtration or by centrifuging.

The methods employed for isolation of the individual acids from the fraction obtained may be:

(i) By column chromatography over silica gel (80–200 mesh), MPLC, preparative HPLC, flash chromatography or the like.

(ii) By combined chemical and chromatographic methods.

Accordingly the following bowellic acids have been isolated from the fraction:

1. B-Boswellic acid of the formula 1

2. 3-acetyl, B-boswellic acid of the formula 2

3. 11-Keto-B-boswellic acid of the formula 3

4. 3-acetyl-11-keto-B-boswellic acid of the formula 4

5. 3a-hydroxyurs-9-12-diene-24-oic acid of the formula 5

6. 2a-3a-dihydroxyurs-12-ene-4-oic acid of the formula 6.

It appears the fraction has the unexpected combined activities of anti-inflammatory, anti-arthritic and anti-ulcerogenic due to the presence of the novel acid in the fraction even in small amounts and also due to the percentage of the constituents as mentioned above.

Further, research work is in the progress to study the synergistic effect of the fraction isolated and also to determine the nature and characteristics of the unidentified compounds present in the fraction.

Detailed pharmacological studies were carried out on the fraction isolated by the process of the present invention in a variety of acute, sub-acute and chronic test models of inflammation and various inflammatory conditions.

Animal studies were carried out in the following laboratory animal test models both acute and chronic in nature.

Acute Test Models

1. Carrangeenan oedema in rats and mice.

2. Histamine oedema in rats.

3. Dextran oedema in rats.

4. Acetic acid induced vascular permeability test in mice.

Sub-Acute Test
  Cotton pellet granuloma in rats.
  Croton oil granuloma in rats.
Chronic Test Models
  Developing adjuvant arthritis in rats.
  Established adjuvant arthritis in rats.
  Formaldehyde induced arthritis in rats.
  Sodium urate gouty arthritis in dogs.
  Bovine serum albumin (BSA) arthritis in rabbits.
  Study on polymorphonuclear leucocyte (PMNL) migration in rats both in vivo and in vitro.
Study on Arthritis Elevated:
  Serum glycoproteins metabolites.
  Serum glycohydrolases metabolites.
  Serum glutamic pyruvic transaminase (SGPT).
  Serum Glutamic oxaloacetic transaminase (SGOT).
  Serum Alkaline phosphatase.
  Serum acid phosphatase.
  Study on pregnant rats.
  Castor oil induced diarrhea in rats.
  Study on cardiovascular system in anaesthetised dogs and rats—B. P., H. R. and E.C.G.
  Study on central nervous system in rats and mice.
  Protection by the mixture of boswellic acids against galactosamine/endotoxin-induced hepatitis in mice.
  Study of leukotriene $B_4$ formation in rat peritoneal neutrophils by extract of the gum resin of Boswellia serrata containing the above said mixture of boswellic acids.

Boswellic acids were found to possess anti-complementary activity. They inhibited in vitro immuno-haemolysis of antibody coated sheep erthrocytes by pooled guinea-pig serum. The reduced immunohaemolysis was found to be due to inhibition of C-3 convertase of the classical complement pathway. In vivo administration of boswellic acids also showed the inhibitory effect in guinea-pig serum [Kapil A and Moza, N. Int. J. Immunopharmac, 14, 1139 (1992)].

Pre Clinical Toxicological and Safety Evaluation
  1. Acute toxicity in rats and mice.
  2. Sub-acute toxicity in rats over 4 weeks.
  3. Chronic toxicity in rats over six months. 4. Chronic toxicity in primates over six months.
Results The fraction isolated by the process of the present invention demonstrated dose related anti-inflammatory activity (AIA) in a battery of test models. In a dose range of 25–200 mg/kg orally, the fraction displayed 25.71 to 47.54% inhibitory action in carrageenan, histamine and dextran induced oedema in rats and mice. The former test is widely employed for its sensitivity to detection of drug of proven value. AIA remained unaltered in adrenalectomised rats indicating its action independent of activation through pituitary-adrenal axis. In acetic acid included vascular permeability test, BA (50–200 mg/kg p.o.) produced 41.94 to 59.53% inhibitory effect with P-value 0.001. In chronic tests of developing adjuvant arthritis, the fraction demonstrated anti-arthritic activity by 32.23 to 54.54% with significant inhibition of secondary lesions i.e., it checked the loss in body weight, nodules on tail and hemorrhagic patches on ears.

The fraction isolated was found to be equally effective in established adjuvant arthritis indicating its possible usefulness as an anti-arthritic agent. Anti-arthritic effect was found to be more marked in chemically induced formaldehyde arthritis in rats. The fraction at dose range of 50–200 mg/kg produced 37.54 to 62.85% inhibitory effect. In sodium urate gouty arthritis in dogs, the mixture of boswellic acids at 100–300 mg/kg decreased the total leucocytes in the aspirated synovial fluid by 20.60–57.41% and checked the development of typical three legged walk as compared to control dogs which evinced pain when made to walk.

In bovine serum albumin (BSA) induced arthritis in rabbits, the fraction at 25, 50 and 100 mg/kg orally, significantly reduced the population of leucocytes in the BSA injected knee. It was found to be equally effective upon local injection into the knee at 5, 10 and 20 mg.

The fraction also significantly inhibits the migration of leucocytes into the pleural cavity, pleurisy induced by carrangeenan and dextran. It displayed no action on haemolysing activity, local irritant or cytotoxic effect as evidenced by dye exclusion test model. The fraction inhibited the arthritis elevated levels of connective tissue metabolites in urinary excretion-urinary hydroxyproline (free, total, nondialysable and dialysable) hexosamine and urinic acid.

The fraction isolated by the process of the present invention demonstrated highly significant protection against galactosamine/endotoxine induced hepatitis in mice.

The invention is described in detail in the examples given below which are provided by way of illustration only, and are not intended to limit the scope of the present invention.

EXAMPLES

Example 1

Isolation of a Fraction Comprising Boswellic Acids of Formulae I through VI and Other Unidentified Compounds from the Gum Resin of Boswellia Serrata.

1 kg crushed granules or the lumps of the gum exudate are extracted in methanol (3 lit) for 12 hrs. The extraction process is repeated twice with 2.5 lit of methanol and residue is discarded. The total extract after filtration is concentrated in vacuo. The red brown syrupy mass (700 g) obtained as above is treated with 3% solution of potassium hydroxide till the pH of 9–10 is attained. The solution is vigorously stirred for 12 hrs till a uniform emulsion is formed. The emulsion is then extracted with three portions (1 liter each) of dichloromethane in a separator. The lower solvent layer is separated and discarded. To the upper aqueous fraction is added dilute hydrochloric acid solution (5%) till the pH of 3–4 is achieved. The precipitated acids are filtered out and washed several times with water till free of mineral acid. The product is then dried in an air oven at 40°–45° to a creamish yellow powder boswellic acid mixture comprising the compounds of the formulae I to VI and the unidentified compounds. The amount of compounds of the formulae I through VI and the unidentified compounds was found to be 51%, 32%, 6%, 5.0%, 1.5%, 1.2% and unidentified compounds 2.5% respectively.

Example 2

Isolation of a Fraction Comprising a Mixture of Boswellic Acids of the Formulae I through VI and Other Unidentified Compounds from the Gum of Boswellic Serrata.

500 gm crushed granules or the lumps of the gum exudate are extracted with ethyl acetate (2 liters) for 24 hours. The extraction is repeated twice with 1.5 lit of ethyl acetate and the residue discarded. The combined extract after filtration is concentrated under vacuum. The syrupy mass (290 g) obtained as above is treated with 3% solution sodium hydroxide till the pH of 9–10 is attained. The solution is vigorously stirred for 10 hrs till a uniform emulsion is formed. The emulsion is then extracted with three portions, each (750 ml) of petroleum ether. The upper solvent layer is separated and discarded. To the lower aqueous layer is added a dilute hydrochloric acid solution (4%) till pH of 3–5 is attained. The precipitated acids are centrifuged or filtered and washed several times with water till neutral to litmus. The product is dried in an oven at 40°–45° C. to a creamish yellow powder (150 g, 30%). The fraction comprising the compounds of the formulae I thought VI and the unidentified compounds in the fraction was found to be 50%, 33%, 6%, 5.5%, 1.5%, 1.0% and 2.5% respectively.

Example 3

Chromatographic Separation of Individual Boswellic Acids of the Formulae I through VI from the Fraction isolated from the Gum of the Plant *Boswellia Serrata*.

10 g of the total boswellic acids mixtures obtained in Example 1 was charged on a silica gel column (250–400 mesh) 250 g. The elution of the column was carried out under nitrogen pressure by hexane/ethyl acetate (80/20–30/70) with gradient elution. The progress of the column was monitored by TLC. After repeated chromatography of the mixtures and combining the pure isolates the following compounds were separated; acetyl boswellic acid of the formula II (2.60 g), B-boswellic of the formula I (3.50 g); 3a-hydroxy-urs-9, 12-diene-24-oic acid of the formula V (0.50 g); acetyl-11-keto-B-boswellic acid of the formula IV (0.50 g); 11-keto-B-boswellic acid of the formula III (0.45 g); 2a, 3a-dihydroxy-urs-12-ene-24-oic acid of the formula VI (0.10 g). Besides three other compounds which could not be identified were also separated in minor amounts. The compound of the formula VI is a new compound isolated for the first from the acidic fractions of gum resin. The structure of the compound of formula VI was assigned on the basis of its spectral data and chemical transformation studies.

Example 4

Chromatographic Separation of Individual Boswellic Acids of the Formulae I through VI from the Fraction Isolated from the Gum Plant *Boswellia Serratia*.

A mixture of 10 g of the boswellic acids obtained in Example 2 was charged on a silica gel column (60 to 120 mesh) 400 g. The elution of the column was carried out by chloroform; methanol was monitored by TLC. After repeated chromatographing the mixtures with same solvent gradients and combining the pure isolates, the following compounds were separated acetyl B-boswellic acid of the formula 2 (2.80 g), B-boswellic acid of the formula 1 (3.20 g); 3a-hydroxyurs-9, 12-diene-24-oic acid of the formula 5 (0.12 g), acetyl, 11-keto-B-boswellic acid of the formula 4 (0.33 g), 11-keto-B-boswellic acid of the formula 3 (0.40 g), 2a, 3a-dihydroxyurs-12-ene-24-oic acid of the formula 6 (0.08 g). Besides these other unidentified compounds which were also isolated in example 3 were also isolated in minor amounts.

Example 5

Separation of Boswellic Acids of the Formulae I through VI by Chemical and Chromatographic Methods.

(a) The fraction of the acid mixture (10 g) as obtained in example 1 is hydrolysed with potassium carbonate (12g) in methanol (100 ml) at 65° C. for 2 hrs. The hydrolysed mixture is filtered and concentrated to one fourth of its original volume. The concentrated extract is refrigerated for 6 hrs and first crop of pure -boswellic acid (3 g) of formula 1 is separated by filtration. The mother liquor is further concentrated, kept overnight and filtered to obtain the second crop of B-boswellic acid (1.0 g). From the remaining mother liquor solvent is evaporated and mixture is subjected to column chromatography over silica gel (60 to 120 mesh) 120 g. The elution is carried out with methanol/chloroform (5/95 to 20/80) with gradient elution and monitoring the progress of column by TLC. The following compounds could be separated by repeated column chromatography. B-boswellic acid of formula I (1.3 g), 11-keto-B-boswellic acid of the formula III (1.00 g) and 2a, 3a-dihydroxy-urs-12-ene-24-oic acid of the formula VI (0.09 g) and other unidentified compounds.

(b) The fraction containing the boswellic acid mixture (10 g) as obtained in example 1 is acetylated in acetic anhydride (35 ml) and pyridine (2 ml) and the mixture is kept overnight in a refrigerator. Acetyl B-boswellic acid of the formula II (3.7 g) which crystallised out is separated by filtration and washing with dilhydrochloric acid and water. The mother liquor is concentrated to one third of its original volume and again refrigerated for 12 hrs to give second crop of the compound of formula II (1.5 g). From the remaining mother liquor the solvent is evaporated under reduced pressure and the mixture is subjected to column chromatography over silica gel (60–120 mesh) 120 g as described in part (a) of this example. The following compounds were separated by repeated chromatography. Acetyl B-boswellic acid of the formula II (1.0 g), 3a-acetoxyurs-9, 12 diene-24-oic acid which was hydrolysed with sodium carbonate in liquor is further concentrated, kept overnight and filtered to obtain the second crop of B-boswellic acid (1.0 g). From the remaining mother liquor solvent is evaporated and mixture is subjected to column chromatography over silica gel (60 to 120 mesh) 120 g. The elution is carried out with methanol/chloroform (5/95 to 20/80) with gradient elution and monitoring the progress of column by TLC. The following compounds could be separated by repeated column chromatography. B-boswellic acid of formula I (1.3 g), 11-keto-B-boswellic acid of the formula III (1.00 g) and 2a, 3a-dihydroxy-urs-12-ene-24-oic acid of the formula VI (0.09 g) and other unidentified compounds.

(b) The fraction containing the boswellic acid mixture (10 g) as obtained in example 1 is acetylated in acetic anhydride (35 ml) and pyridine (2 ml) and the mixture is kept overnight in a refrigerator. Acetyl B-boswellic acid of the formula II (3.7 g) which crystallised out is separated by filtration and washing with dilhydrochloric acid and water. The mother liquor is concentrated to one third of its original volume and again refrigerated for 12 hrs to give second crop of the compound of formula II (1.5 g). From the remaining mother liquor the solvent is evaporated under reduced pressure and the mixture is subjected to column chromatography over silica gel (60–120 mesh) 120 g as described in part (a) of this example. The following compounds were separated by repeated chromatography. Acetyl B-boswellic acid of the formula II (1.0 g), 3a-acetoxyurs-9, 12 diene-24-oic acid which was hydrolysed with sodium carbonate in methanol (8%), to furnish 3a-hydroxyurs, 9, 12-diene-24-oic acid of the formula IV (0.085 g); acetyl 11-keto-B-boswellic acid of the formula VI (1.00 g) and 2a, 3a-diacetoxy-urs-12-ene-24-oic acid which was similarly hydrolysed to give 2a, 3a-dihydroxy-urs-12-ene-24-oic acid of the formula VI (0.10 g).

What is claimed is:

1. A novel composition exhibiting anti-inflammatory and antiulcerogenic activities, said composition comprising a mixture of boswellic acids of the formulae I through VI identified as follows:

Formula I

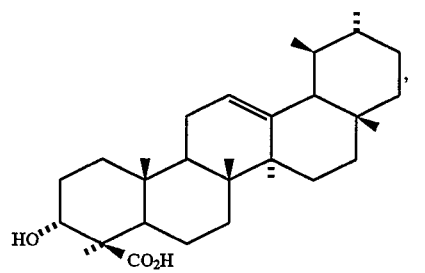

Formula II

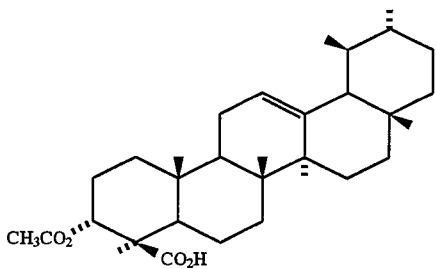

Formula III

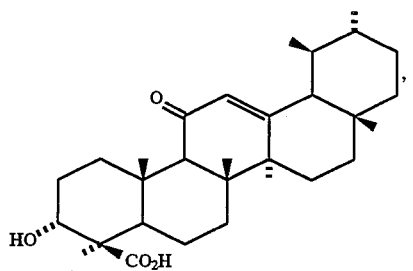

Formula IV

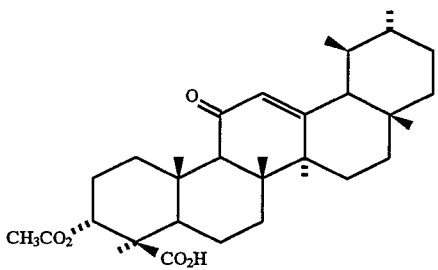

Formula V

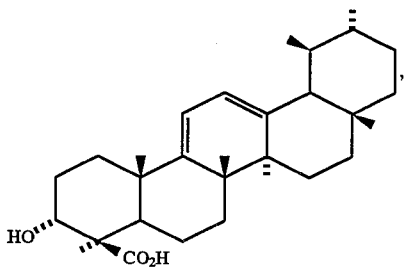

Formula VI

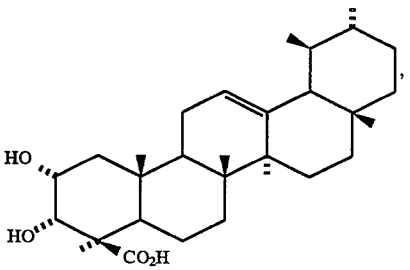

said composition comprising 35% to 55% by weight of a compound of Formula I, 25% to 45% by weight of a compound of Formula II, 4% to 14% by weight of a compound of Formula III, 3% to 13% by weight of a compound of Formula IV, 1% to 3% by weight of a compound of Formula V, and 1% to 3% by weight of a compound of Formula VI.

2. A boswellic acid compound exhibiting anti-inflammatory antiathritic and antiulcerogenic activities and having the structural formula:

Formula VI

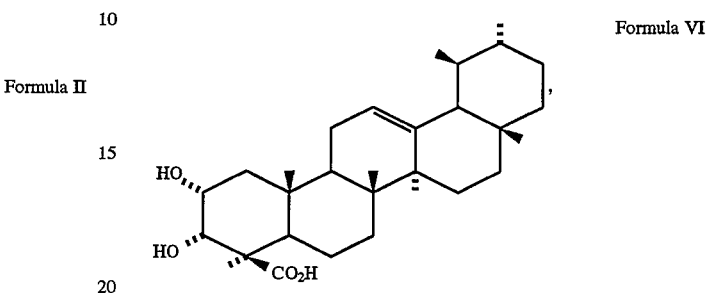

said compound being produced by separating said compound from a composition comprising:

Formula I

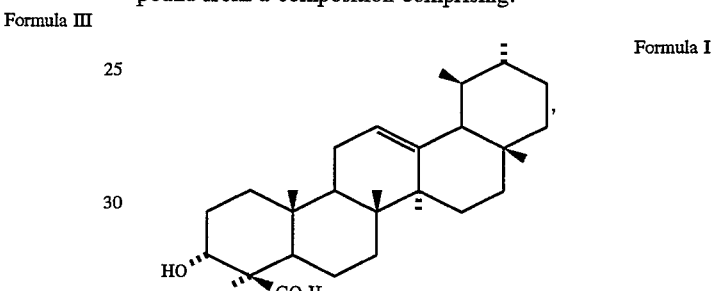

Formula II

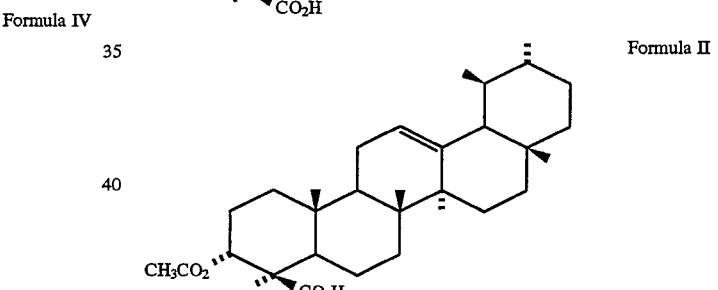

Formula III

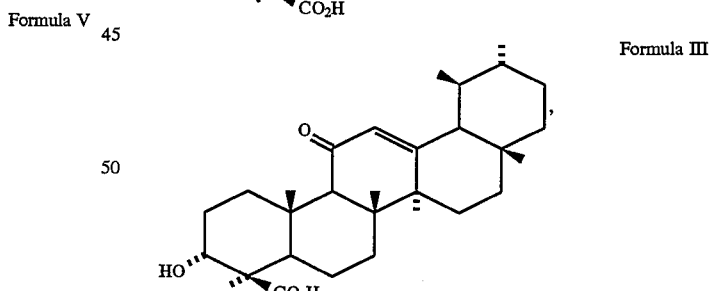

Formula IV

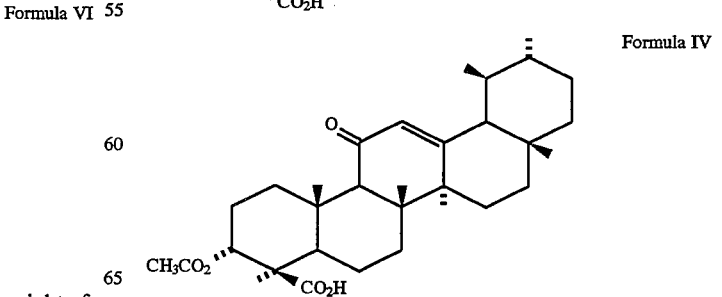

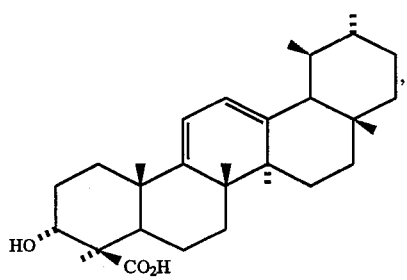

Formula V

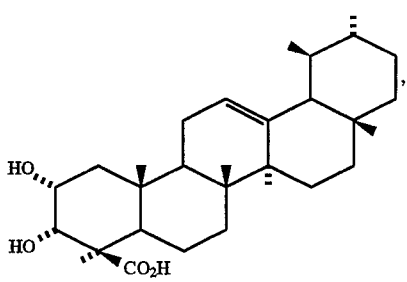

Formula VI said composition comprising 35% to 55% by weight of a compound of Formula I, 25% to 45% by weight of a compound of Formula II, 4% to 14% by weight of a compound of Formula III, 3% to 13% by weight of compound of Formula IV, 1% to 3% by weight of a compound of Formula V, and 1% to 3% by weight of a compound of Formula VI.

3. A process for the isolation of a boswellic acid fraction exhibiting anti-inflammatory and antiulcerogenic activities, said fraction comprising a mixture of boswellic acids, and optionally isolating individual boswellic acids from said fraction, said process comprising the steps of:

(a) crushing the lumps of the gum resin of *Boswellia serrata* and extracting the crushed lumps with a polar solvent to provide an extract;

(b) filtering or centrifuging said extract to remove insoluble material from said extract;

(c) vacuum distilling the extract untill a reddish brown syrupy mass is obtained;

(d) basifying the syrupy mass with an aqueous solution of an alkali to provide a solution having a pH in the range of 9 to 10;

(e) extracting the solution with chlorinated or non-polar solvents to provide an aqueous layer, and acidifying the aqueous layer with mineral acid to a pH in the range of 3–5 to provide a precipitate comprising boswellic acids;

(f) washing the precipitate with water to provide said fraction being neutral to litmus;

(g) drying the fraction to provide a dry fraction, said dry fraction comprises:

(a) 35 to 55% by weight of a compound of the formula:

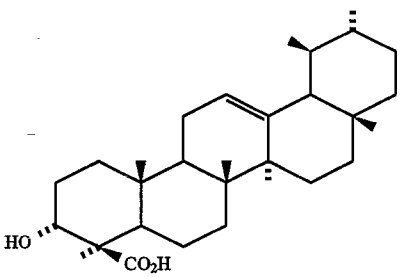

I (b) 25 to 45% by weight of a compound of the formula:

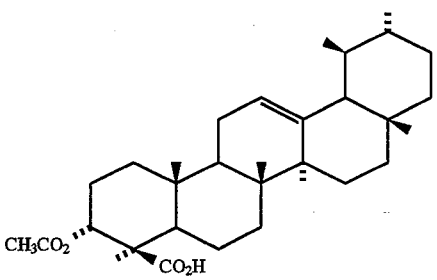

II (c) 4 to 14% by weight of a compound of the formula:

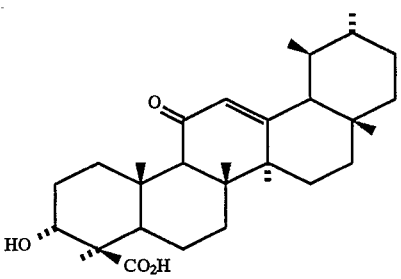

III (d) 3 to 13% by weight of a compound of the formula:

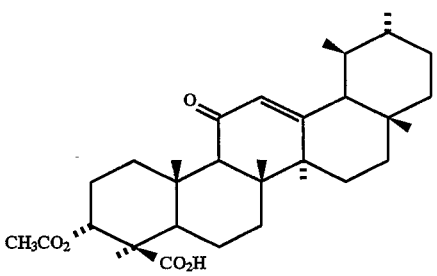

IV (e) 1 to 3% of a compound of the formula:

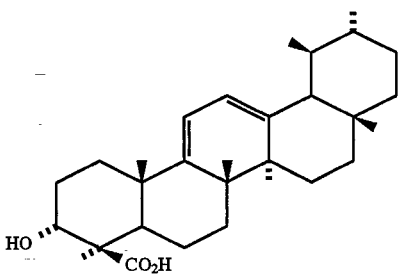

V and, (f) 1 to 3% by weight of a compound of the formula:

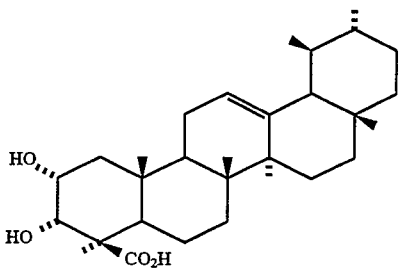

VI

4. A process as claimed in claim 3 wherein the gum is extracted in polar solvent selected from the group consisting of methanol, ethanol, butanol, ethyl acetate, acetone and the like, and mixtures thereof.

5. A process as claimed in claim 3 wherein the alkali solution used for extracting the concentrated extract obtained in step (a) is selected from sodium hydroxide, potassium hydroxide, lithium hydroxide and combination thereof.

6. A process as claimed in claim 3 wherein non-polar solvent used to extract the aqueous portion is selected from hexane, heptane, benezene, dichloromethane, chloroform and combinations thereof.

7. A process as claimed in claim 3 wherein the acidification in step (e) is effected at pH 3–5 by using dilute mineral acid.

8. A process as claimed in claim 3 wherein the fraction isolated is dried in air oven at a temperature in the range of 40°–45° C.

9. A process as claimed in claim 3 wherein the dry fraction is separated into individual boswellic acids by chromatographic methodology selected from the group consisting of column chromatography employing silica gel or alumina, mp liquid chromatography, flash chromatography, preparative pH liquid chromatography, and combinations thereof.

* * * * *